United States Patent [19]

Earl et al.

[11] Patent Number: 6,039,957
[45] Date of Patent: *Mar. 21, 2000

[54] OLIGOMERIC HIV-1 ENVELOPE GLYCOPROTEINS

[75] Inventors: Patricia L. Earl, ChevyChase; Christopher C. Broder, Rockville, both of Md.; Robert W. Doms, Berwyn, Pa.; Bernard Moss, Bethesda, Md.

[73] Assignee: United States of America, as represented by the Department of Health and Human Services, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/805,889

[22] Filed: Mar. 3, 1997

Related U.S. Application Data

[62] Division of application No. 08/165,314, Dec. 10, 1993, abandoned.

[51] Int. Cl.$^7$ .................................................. A61K 39/21
[52] U.S. Cl. .................................... 424/208.1; 424/187.1
[58] Field of Search .......................... 424/148.1, 187.1, 424/204.1, 208.1; 435/70.21, 172.2, 339.1, 449, 451, 452; 530/388.35

[56] References Cited

U.S. PATENT DOCUMENTS 4,725,669  2/1988  Essex et al. ............................ 530/322

FOREIGN PATENT DOCUMENTS 9206113  4/1992  WIPO .

OTHER PUBLICATIONS

Greene, Warner C.; AIDS and the Immune System; Life, Death and the Immune System; Scientific American, Sep. 1993; pp. 97–105.
Berman, Phillip W., et al.; Protection of chimpanzees from infection by HIV–1 after vaccination with recombinant glycoprotein gp120 but not gp160; NATURE, vol. 345; Jun. 14, 1990; pp. 622–625.
Berman, Phillip W., et al.; Expression and Immunogenicity of the Extracellular Domain of the Human Imminodeficiency Virus Type 1 Envelope Glycoprotein, gp160; Journal of Virology, 63:8; Aug. 1989, pp. 3489–3498.
Earl, et al. (1992) Multimeric CD4 binding exhibited by human and simian immunodeficiency virus envelope protein dimers. Journal of Virology 5610–5614.
Kieny, et al. (1988) Improved antigenicity of the HIV env protein by cleavage site removal. Protein Engineering 2(3):219–225.
Marasco, et al. Design, intracellular expression, and the activity of a human anti–human immunodeficiency virus type 1 gp120 single–chain antibody. Proc. Natl. Acad. Sci. 90:7889–7893.
Nakamura, et al. (1992) Monoclonal antibodies to the extracellular domain of HIV–1 IIIB gp160 that neutralize infectivity, block binding to CD4, and react with diverse isolates. Aids Research and Human Retroviruses 8(11).
Pasquali, et al. (1990) Immunogenicity and epitope mapping of a recombinant soluble gp160 of the human immunodeficiency virus type 1 envelope glycoprotein. Aids Research and Human Retroviruses 6(9).
Steimer, et al. (1991) Neutralization of divergent HIV–1 isolates by conformation–dependent human antibodies to gp120. Science 254:105–108.
Seaver, S. (1994) Monoclonal antibodies in industry: more difficult than originally thought. Gen. Eng. News pp. 10, 21.
Earl et al, *Proc. Natl. Acad. Sci. USA* 87:648–652, Jan. 1990.
Earl et al., *J. Virol.* 65(1):31–41, Jan. 1991.
Galfre et al., Meth. Enzymol. 73:3–46, 1981.

*Primary Examiner*—Robert D. Budens
*Attorney, Agent, or Firm*—Knobbe, Martens, Olson & Bear, LLP

[57] ABSTRACT

The present invention relates to methods for producing recombinant HIV-1 envelope (env) oligomers for use as immunogens. When gp140 oligomeric glycoproteins were purified by sucrose velocity gradient sedimentation, and then used to immunize mice, the resulting humoral immune response was skewed toward the production of antibodies that recognize conformation-dependent epitopes on the HIV-1 env protein. Assays for HIV-1 infections are described, as well as immonogens for vaccinating against HIV-1 infection.

5 Claims, 4 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

AACATTACAC AAGCTTAATA CACTC                                                25

(2) INFORMATION FOR SEQ ID NO:2:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CCCCCGCGGT TATTATTTTA TATACCACAG CCAATTTGT                                 39

(2) INFORMATION FOR SEQ ID NO:3:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

GTGCTAAGGA TCCGTTCACT AATCG                                                25

(2) INFORMATION FOR SEQ ID NO:4:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

TAATAACCGC GGGGGTTATT CATAATGATA GTAGGAGGC                                 39

(2) INFORMATION FOR SEQ ID NO:5:

(i) SEQUENCE CHARACTERISTICS:
           (A) LENGTH: 22 amino acids

-continued

```
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

Cys Asn Thr Arg Lys Ser Ile Arg Ile Gln Arg Gly Pro Gly Arg Ala
1               5                   10                  15

Phe Val Thr Ile Gly Lys
            20

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

Tyr Asn Lys Arg Lys Arg Ile His Ile Gly Pro Gly Arg Ala Phe Tyr
1               5                   10                  15

Thr Thr Lys Asn Ile Ile Gly
            20
```

OLIGOMERIC HIV-1 ENVELOPE GLYCOPROTEINS

This application is a divisional of U.S. patent application Ser. No. 08/165,314, filed Dec. 10, 1993 (abandoned).

FIELD OF THE INVENTION

The present invention relates to the use of recombinant proteins to stimulate an immune response in a mammal. Specifically, the present invention describes methods for producing and purifying genetically engineered HIV-1 gp140 glycoprotein oligomers that can be used as immunogens.

BACKGROUND OF THE INVENTION

The HIV-1 envelope (env) glycoprotein is a structurally complex integral membrane protein that targets the virus to CD4 positive cells and mediates the fusion between the viral envelope and the cellular membrane. This glycoprotein also harbors antigenic determinants that are recognized by neutralizing antibodies.

The two recognized categories of antibodies that are capable of neutralizing HIV-1 infection include: those that recognize determinants in the V3 loop of gp120 and those that block the gp120-CD4 interaction by binding to conserved regions of gp120. Antibodies directed against the V3 loop generally recognize epitopes formed by a short continuous sequence and are usually referred to as conformation-independent. These conformation-independent antibodies can be elicited by immunization with either peptides or denatured env protein subunits. Extensive antigenic variation in the V3 domain of the env protein restricts the neutralizing activity of anti-V3 loop antibodies to closely related strains of HIV-1. Hence, antibodies capable of neutralizing infection by one strain of HIV-1 may not effectively neutralize infection by a different strain of HIV-1.

In contrast, antibodies to epitopes that are sensitive to the conformation of the protein are typically more broadly neutralizing. Antibodies to these conformation-sensitive epitopes are referred to herein as "conformation-dependent" antibodies. Conformation-dependent antibodies that block CD4 binding, for example, recognize conserved, discontinuous, conformational epitopes in gp120. These antibodies are broadly neutralizing and have been shown to comprise a significant fraction of the total neutralization activity present in HIV-1 infected human sera. In addition, there is evidence that neutralizing antibodies may also be directed against conformationally-dependent epitopes on gp120 (Steimer et al., Science, 254:105 (1991)).

Newly synthesized gp160 monomers noncovalently associate to form higher order oligomeric structures. The association of two env monomers to form a dimer is the most elemental such structure. A larger structure that is believed to be composed of a dimer of dimers, or four monomers, can also form. The ectodomain of gp41 is required for efficient oligomerization of dimers and tetramers (Earl et al., Proc. Natl. Acad. Sci. USA 87:648 (1990); Earl and Moss, AIDS Res. 9:589–594 (1993)).

Given its antigenic nature, the use of recombinant gp160 or derivatives thereof as immunogens represents an attractive vaccine strategy. However, the attempts that have been made to date in this regard have all suffered one or another deficiency. To the extent that humoral immune responses against various gp160 immunogens have been analyzed, none satisfactorily stimulates the broadly neutralizing antibodies that would be required of an effective HIV-1 vaccine. Hence, there remains a need for a vaccine composition that can stimulate the production of broadly neutralizing antibodies against various strains of HIV-1.

SUMMARY OF THE INVENTION

One embodiment of the present invention relates to a method of producing conformation-dependent antibodies against HIV. This method comprises: 1) obtaining recombinant gp140 protein, wherein the gp140 protein retains its oligomeric structure, 2) administering to an mammal the gp140 protein so that the mammal produces antibodies against the oligomeric structure of the gp140. Preferably the administration is either intradermal, intramuscular, intraperitoneal or intravenous. Alternatively, the mammal is either a mouse, a rat, a cow, a sheep or a rabbit. More preferably, the obtaining step includes running the gp140 protein through a sucrose gradient.

Another embodiment of the present invention is a method of preventing an HIV infection in a mammal. First, a mammal at risk for HIV infection is identified. Following identification, the mammal is administered a pharmaceutically effective amount of gp140, wherein the gp140 protein has an oligomeric structure. Preferably, the effective amount of gp140 is in the range of 10–10,000 $\mu$g/kg body mass. More preferably, the gp140 has been isolated from a sucrose gradient prior to administration.

Yet another embodiment of the present invention is a method of diagnosing a HIV infection in a mammal. This method comprises isolating body fluid from a mammal at risk for an HIV infection, wherein the infection produces HIV-specific epitopes in the body fluid. Next, the body fluid is contacted with antibodies having specificity for the oligomeric structure of gp140. Binding of the antibodies to the HIV-specific epitopes in the body fluid is then detected, wherein detectable binding indicates the presence of an HIV infection. Advantageously, the body fluid is blood and the antibodies were raised against the oligomeric structure of gp140. Advantageously, the antibodies are monoclonal, and even more preferably, the antibodies are labelled. The label can be radioactive, fluorescent or enzymatic. In this embodiment the detecting step can be an ELISA.

Still another embodiment of the present invention are isolated antibodies against the oligomeric structure of gp140. These antibodies can be produced by: obtaining recombinant gp140 protein, wherein the gp140 protein retains its oligomeric structure; administering to a mammal the gp140 protein so that the mammal produces antibodies against the oligomeric structure of the gp140; and isolating the antibodies produced against the oligomeric structure of gp140, the antibodies being conformationally-dependent. Advantageously, the antibodies are an IgG isotype and the obtaining step involves running the gp140 protein through a sucrose gradient.

A final embodiment of the present invention is a method of treating a patient having an HIV-1 infection comprising administering to the patient a pharmaceutically effective concentration of an antibody against the oligomeric form of gp140.

Figure 1A:
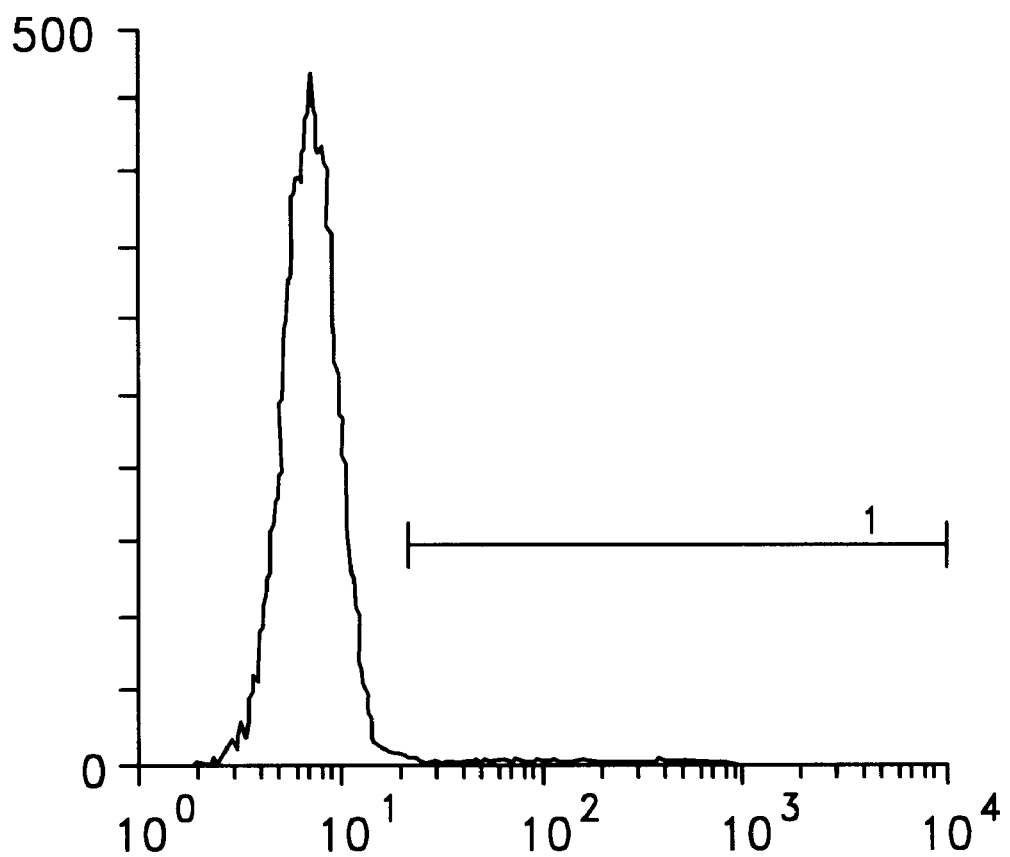
FIGS. 1A–1D show the results of a FACS sort. The horizontal axes represents fluorescence intensity while the vertical axes represents cell number.
Figure 1B:
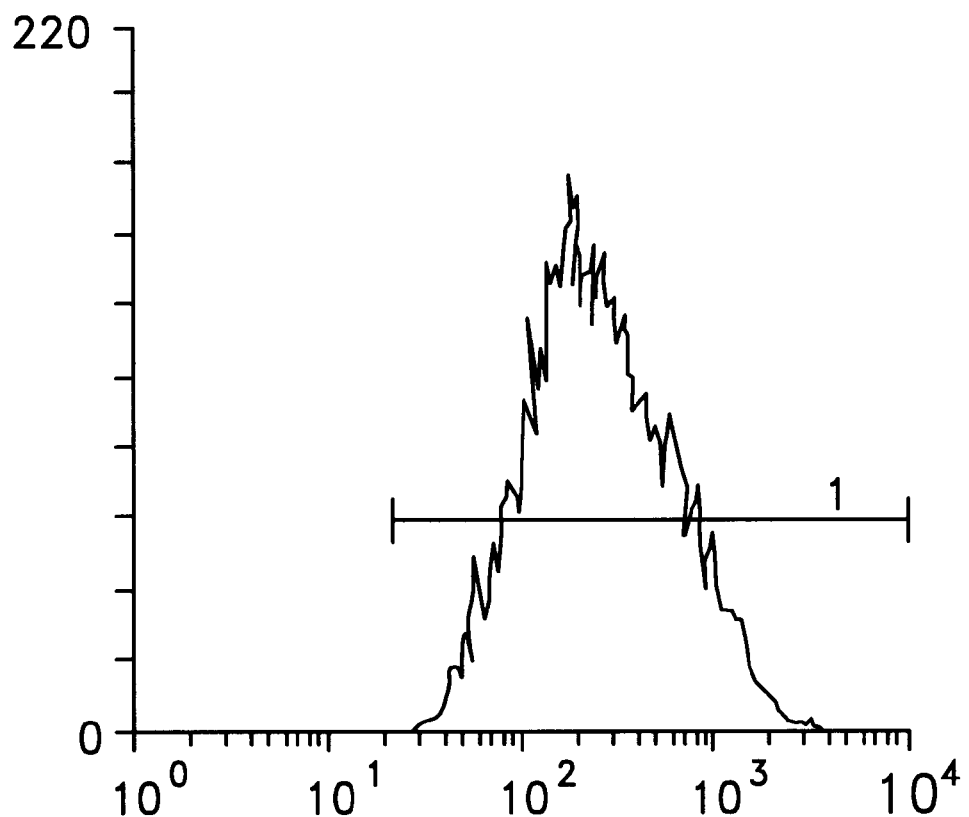

The antibodies used in the experiments summarized in FIGS. 1A–1D were a control mouse IgG, anti-gp120 monoclonal antibody 110.4, anti-gp120 monoclonal antibody D34 and anti-gp41 monoclonal antibody D6, respectively.

DETAILED DESCRIPTION OF THE INVENTION

We have discovered that recombinant HIV-1 env proteins can be produced and purified in such a way that the humoral immune response to these immunogens exhibits a bias toward conformation-sensitive epitopes, thereby producing conformation-dependent antibodies to these proteins.

Significantly, sera from HIV-1 infected individuals is also known to contain high titers of neutralizing antibodies that are reactive against conformation sensitive epitopes. Our discovery therefore provides a means by which immunization with an env subunit preparation can be used to recapitulate some aspects of the immune response that are observed in individuals who have been infected with viable HIV-1.

The recombinant env glycoprotein that provided the advantageous immune response was modified in two ways. First, the proteolytic cleavage recognition site that ordinarily facilitates separation of the gp120 and gp41 subunits was eliminated by site directed mutagenesis. This mutation ensured that a single glycoprotein species was produced that exhibited structural features of both gp120 and gp41. Furthermore, the presence of gp41 amino acid sequences provided a means by which monomers could associate into higher order structures. The second modification to the env glycoprotein was the introduction of stop codons just upstream of the gp41 transmembrane domain. This latter modification allowed the env glycoprotein to be produced in a secreted form. Hence, the recombinant HIV-1 env immunogen described in the present invention is a secreted molecule with an amino acid sequence characteristic of both gp120 and gp41. This recombinant env glycoprotein has a molecular weight of 140 kDa, and so has been termed "gp140."

Several lines of evidence suggested that secreted, oligomeric gp140 would reflect the native env structure. First, the protein was efficiently secreted. Since misfolded molecules are typically retained and degraded in the endoplasmic reticulum, it was unlikely that the folded structure of gp140 was grossly aberrant. Second, gp140 efficiently bound soluble CD4 (sCD4) and the conformation-dependent anti-gp120 monoclonal antibody (MAb), F105. Since the CD4 and F105 epitopes on gp120 are discontinuous in nature, our findings indicated the gp120 portion of the molecule exhibited structural features that were characteristic of the native conformation. The strongest evidence that purified gp140 accurately reflected native env structure came from analysis of anti-gp140 antibodies. The great majority of MAbs raised against oligomeric gp140 recognized env proteins on the surface of cells chronically infected with HIV-1. More than half (79 of 138) of the MAbs that were tested recognized conformational epitopes found on either gp120 or gp41.

These findings demonstrated that an oligomeric gp140 immunogen could be used according to the methods described below to elicit antibodies against conformational epitopes on HIV-1. The large number of MAbs obtained having specificity for conformational epitopes using the process defined below indicated that oligomeric gp140 elicited a qualitatively different immune response than monomeric protein (whether native or denatured). Our findings show that it is possible to produce and purify a soluble, oligomeric form of env which reflects the native structure of the wild-type protein.

The secreted oligomeric HIV-1 env proteins that were used as immunogens in our procedures were produced by recombinant vaccinia viruses, vPE12B and vCB-14. Both of these virus constructs express genes that encode mutated env glycoproteins. The protein coding sequences in these constructs were truncated after amino acid 678 (Lys), just before the transmembrane domain so as to result in 140 kDa env molecules (gp140). To prevent dissociation of gp120 from the gp41 ectodomain fragment during purification, a deletion was made in the region of the env gene that encoded the amino acids at the gp120-gp41 cleavage site. In *J. Virology* 65:31 (1991), Earl et al. showed that this mutation, when introduced into the full length env gene, yielded a non-cleaved form of env that efficiently folds, assembles, is transported to the plasma membrane and can bind CD4. A synthetic early/late vaccinia virus promoter was utilized to drive high levels of gene expression.

Example 1 illustrates the construction of recombinant vaccinia viruses that express modified HIV-1 env glycoproteins.

EXAMPLE 1

Construction of a Recombinant Vaccinia Virus for Expression of a Truncated HIV-1 env Protein Two recombinant vaccinia viruses were constructed for production of soluble, secreted, HIV-1 env glycoprotein gp140. The BH8 HIV-1 isolate (Genbank accession number K02011) was used as the source of the env gene in these constructions. Nucleotide numbers referenced below correspond to this sequence. For construction of both recombinant viruses, two translation termination codons were inserted after nucleotide 2034, just prior to the transmembrane domain of gp41 after amino acid residue 678. These mutagenesis reactions were performed using a two-step polymerase chain reaction (PCR) protocol as described by Ho, et al. in *Gene* 77:51 (1989). Numbering of amino acids started at the beginning of the open reading frame and thus includes the signal peptide. In the first step, two DNA fragments with overlapping ends were synthesized. These fragments spanned a region of the env gene from the HindIII restriction site (nucleotide 2128), through the transmembrane coding region, to the BamHI restriction site (nucleotide 2462). One fragment was generated in a PCR reaction with a first primer (a) 5'-AACAATTACACAAGCTTAATACACTC-3' (Seq. I.D. No: 1) containing the HindIII restriction site and a second primer (b) 5'-CCCCCGCGGTTATTATTTTATATACCACAGCCA ATTTGT-3' (Seq. I.D. No: 2) containing the translation termination codons. The other fragment was generated with oligonucleotide (c) 5'-GTGCTAAGGATCCGTTCACTAATCG-3' (Seq. I.D. No: 3) containing the BamHI restriction site in conjunction with (d) 5'-TAATAACCGCGGGGGTTATTCATAATGATAGT AGGAGGC-3' (Seq. I.D. No: 4). These two amplified fragments were then used together in a second PCR reaction along with oligonucleotides (a) and (c), to generate a 372 base pair fragment. This fragment was digested with HindIII and BamHI and exchanged with the analogous fragment in the env gene of pSC60 (S. Chakrabarti, unpublished), a plasmid which contains the entire env gene under control of a synthetic early/late vaccinia virus promoter. The resulting plasmid, pCB-14, thus contained the env gene truncated after amino acid 678. The proteolytic cleavage sites between gp120 and gp41 were removed by restriction fragment substitution of a 575 base pair SspI-HindIII fragment between nucleotides 1553 and 2128 with the analogous fragment from the plasmid, pPE12, which has been described by Earl et al., in *J. Virology* 65:31 (1991), to generate pPE12B. The plasmid pPE12 contained the env gene from which 12 amino acids, including the primary and secondary cleavage sites, had been removed. Hence, plasmids pCB-14 and pPE12B were used to generate recombinant vaccinia viruses (vCB-14 and vPE12B) which expressed cleavable and non-cleavable secreted gp140 molecules, respectively.

Several other recombinant vaccinia viruses were also used. vPE16 has been described by Earl et al. in *J. Virology* 64:2448 (1990) and expresses wild type gp160 under control of the vaccinia virus 7.5% promoter. vSC60 expresses wild type gp160 under control of the vaccinia virus synthetic early/late promoter. vPE12 expresses a noncleavable form of gp160; vPE8 expresses gp120; and the series VPE17, vPE18, vPE20, vPE21, and vPE22 (Earl et al., *J. Virology* 65:31 (1991)) express C-terminally truncated env glycoprotein molecules. vSC64 expresses a chimeric env glycoprotein molecule consisting of HIV-2 gp120 and HIV-1 gp41 (S. Chakrabarti, unpublished). vCB-5 which has been described by Broder and Berger in *J. Virology* 67:913 (1993), expresses soluble CD4 (372 amino acid residues). Finally, the plasmid, pPE63, which has been described by Earl and Moss in *AIDS Res. and Hum. Retro.* 9:589 (1993) expresses a truncated env glycoprotein via the hybrid vaccinia/T7 system.

The protein made by vCB-14 infected cells was secreted in both cleaved and non-cleaved forms while that expressed by vPE12B was recovered primarily as non-cleaved gp140.

To produce oligomeric gp140 glycoproteins for use as immunogens, BS-C-1 monolayers (ATCC CCL26) were infected with vPE12B. The secreted gp140 was purified from the culture medium using a two-step procedure as described below in Example 2.

EXAMPLE 2

Purification of Secreted Recombinant HIV-1 env Glycoprotein gp140 for Immunizations Typically, 40 confluent 150 cm$^2$ flasks, containing approximately 1.5×10$^7$ BS-C-1 cells per flask, were infected with vPE12B at a multiplicity of infection of 10. Two hours after infection, the monolayers were washed three times with phosphate buffered saline (PBS) to remove free virus particles and then overlaid with the commercially available reduced serum media, OPTI-MEM (Gibco, Grand Island, N.Y.). After 24 to 36 hours, the medium was harvested and culture debris was removed by centrifugation for 30 minutes at 12,000 rpm. TRITON-X-100 was then added to 0.5% final concentration. Glycoproteins were then purified by lentil lectin-Sepharose (Pharmacia, Piscataway, N.J.) chromatography as follows: The pooled culture supernatant containing secreted gp140 was cycled continuously over a 13 cm×1 cm column overnight. The column was washed with PBS containing 10 mM Tris-HCl pH 8.0, 0.3 M NaCl, 0.5% TRITON-X-100 (10 column volumes) followed by PBS containing 10 mM Tris-HCl pH 8.0 (2 column volumes). Glycoproteins were eluted with 0.5 M methyl alpha-D-mannopyranoside in PBS containing 10 mM Tris-HCl pH 8.0 (3 column volumes) and concentrated 20 to 30× in CENTRICON microconcentrators. This step resulted in elimination of most contaminating proteins. The concentrated material was loaded onto 5–20% sucrose gradients and centrifuged 20 hours in an SW40 rotor at 40,000 rpm, 4° C. After fractionation of the gradients, aliquots were analyzed by sodium dodecyl sulfate polyacrylamide gel electrophoresis (SDS-PAGE) followed by Western blotting using a rabbit polyclonal antisera to HIV-1 gp160 (R160) described by Willey et al., in *Virology* 184:319 (1991) and $^{125}$I-labeled protein A (Amersham). The results of the Western blot showed a band corresponding to a 140 kDa molecular weight protein. The majority of the gp140 glycoprotein was in dimeric and higher order forms. A minor peak that contained monomeric gp140 and gp120 was also obtained. Fractions containing monomeric, dimeric, and tetrameric env glycoprotein were separately pooled and concentrated.

To verify the oligomeric status of each pooled fraction, aliquots were cross-linked with 1 mM ethylene glycolbis (succinimidylsuccinate) (EGS) (Pierce, Rockford, Ill.) and analyzed by SDS-PAGE (4%) and Western blotting with R160 as described by Earl et al., in *Proc. Natl. Acad. Sci. USA* 87:648 (1990). The Western blotting results confirmed that the dimeric and tetrameric gp140 fractions were cross linked into dimers and larger forms, respectively, whereas monomeric gp140 was not cross-linked into larger molecular weight species. The gradient separations were judged to be efficient, as there was no evidence for cross contamination between the monomer, dimer and tetramer fractions. Analysis of the Coomassie staining pattern of each sucrose gradient peak indicated that gp140 was the predominant band in all three preparations.

Example 3 illustrates how mice can be injected with the isolated gp140 glycoproteins to stimulate an anti-env immune response. Further, Example 3 describes the production of hybridomas from the spleen cells of the immunized mice.

EXAMPLE 3

Immunization of Mice and Production of Hybridomas

A.SW/SnJ mice (Jackson Laboratories, Bar Harbor, Me.) were immunized with either monomeric (2 mice), dimeric (3 mice), or tetrameric (4 mice) gp140 preparations with RIBI adjuvant (RiBi Immunochem Research Inc., Hamilton, Mont.) as recommended by the supplier. A preliminary test indicated that emulsification of the preparations in this adjuvant did not affect the oligomeric state of the env glycoprotein as shown by chemical cross-linking followed by Western blot analysis. Mice were inoculated at 3 week intervals with 15–20 µg of purified HIV-1 env glycoprotein per mouse (½ subcutaneously and ½ intraperitoneally). Serum collected from each animal after the first inoculation efficiently reacted with gp140 as assayed by immunoprecipitation. The serum was also reactive with gp160, gp120, and gp41 as assayed by Western blotting. Mice receiving monomeric and dimeric gp140 preparations were inoculated three times while mice receiving tetrameric gp140 were inoculated four times.

Three days after the final inoculation, mice were sacrificed and the spleens harvested and prepared for cell fusion using standard methods. Splenocytes were fused with Sp2/0 Ag14 myeloma cells (ATCC CRL1581) with polyethylene glycol using a modification of the method of Gefter et al., described in *Somat. Cell Genet.* 3:231 (1977). Following polyethylene glycol fusion, the cell preparations were distributed in 96-well plates at a density of 10$^5$ cells per well, based on the number of Sp2/0 partner cells, and selected in Ivscove's minimal essential medium (IMEM) supplemented with hypoxanthine/aminopterin/thymidine (HAT medium), 10% FCS (Hyclone Laboratories, Hazelton, Mont.), and 100 units of IL-6 per ml (Boehringer Mannheim Biochemicals, Indianapolis, Ind.). No feeder cell cultures were employed. The medium was replaced with fresh HAT-supplemented IMEM approximately 10 days after plating.

To identify hybridomas producing MAbs that were capable of recognizing conformation-dependent epitopes, hybridoma supernatants were tested for the ability to immunoprecipitate radioiodinated, gradient purified oligomeric or monomeric gp140. Example 4 illustrates the method used to prepare the radiolabeled env reagents, and to screen the various MAbs for binding activity.

EXAMPLE 4

Screening MAbs for gp140 Oligomer Binding

Preparations of purified monomeric, dimeric, or tetrameric gp140 glycoproteins (50 μg) were labeled with $^{125}I$ by the chloramine T method using IODOBEADS (Pierce Chemical) as described by Markwell in *Anal. Biochem.* 125:427 (1982). Radiolabeled glycoproteins were separated from free iodine by passage over a G-25 Sepharose column, and stored at 4° C. Typically, 1.0 μg of gp140 contained approximately 1 to $2\times10^6$ CPM. Iodination of gp140 preparations did not disrupt their oligomeric structure as determined by cross-linking with 1 mM EGS and analysis by SDS-PAGE (4%) and Western blotting.

Twelve days after plating, the supernatants from all wells containing a hybridoma colony were screened by immunoprecipitation with radioiodinated gp140 preparations. A 100 μl sample of culture supernatant was incubated with 100 μl of PBS containing 0.5% TRITON X-100, 0.5% NONIDET P-40, radioiodinated gp140 (approximately 100,000 CPM), and 4 μg of rabbit anti-mouse IgG (Calbiochem, La Jolla, Calif.) for 1 hour at room temperature in microcentrifuge tubes. The oligomeric forms of gp140 used for screening each set were the same as that used for immunization. Protein A Sepharose beads (100 μl of a 20% suspension) were then added and tubes rocked for 30 minutes. The Protein A Sepharose beads we used in our procedures were obtained from Pharmacia (catalog number 17-0780-01). The Sepharose beads were centrifuged and the pellets were washed once with PBS containing 0.5% TRITON-X-100 and 0.5% NP-40. The tubes were counted in a Beckman Gamma 5500B counter. The MAb 902, which binds the V3 loop of gp120, described by Chesebro and Wehrly, in *J. Virology* 62:3779 (1988), and polyclonal rabbit antibody R160, which identifies all forms of env, were included as positive controls. Culture supernatant from an irrelevant hybridoma was included as a negative control.

The results of this screening procedure were unambiguous. Supernatants from negative wells precipitated<1000 CPM of gp140 while most positive supernatants immunoprecipitated>20,000 CPM. During the initial screening, random samples that were deemed positive were analyzed by SDS-PAGE to ensure that gp140 was indeed immunoprecipitated. No false positives were detected. Altogether, 190 hybridomas from 9 mice in 5 fusion experiments were strongly positive using this assay. Of these, 180 were still positive after expansion. Of this number, 138 were cloned by limiting dilution using standard methods. Of this number only 15 were derived from mice immunized with monomeric gp140.

Since the mice used as spleen donors for hybridoma production had been immunized with a non-cleavable, truncated form of env it was important to demonstrate that the MAbs recognized the authentic HIV-1 env molecule. To do this, approximately 90% of the MAbs were screened by FACS analysis for the ability to recognize naturally occurring env on the surface of cells chronically infected with HIV-1 IIIB. Example 5 describes the procedures that were used to carry out these tests.

EXAMPLE 5

Identification of MAbs that Recognize Native HIV-1 env

Human T cells ($1\times10^6$/50 μl) chronically infected with HIV-1 (IIIB) were incubated with the various hybridoma supernatants described above. After 30 minutes at 4° C., the cells were washed twice with PBS containing 1% bovine serum albumin, incubated with goat anti-mouse-fluorescein isotiocyanate for 30 minutes at 4° C. and then washed 2 times. The cells were resuspended in 1 ml of 4% paraformaldehyde and analyzed with a fluorescence-activated cell sorter (FACScan; Becton Dickinson).

Figure 1C:
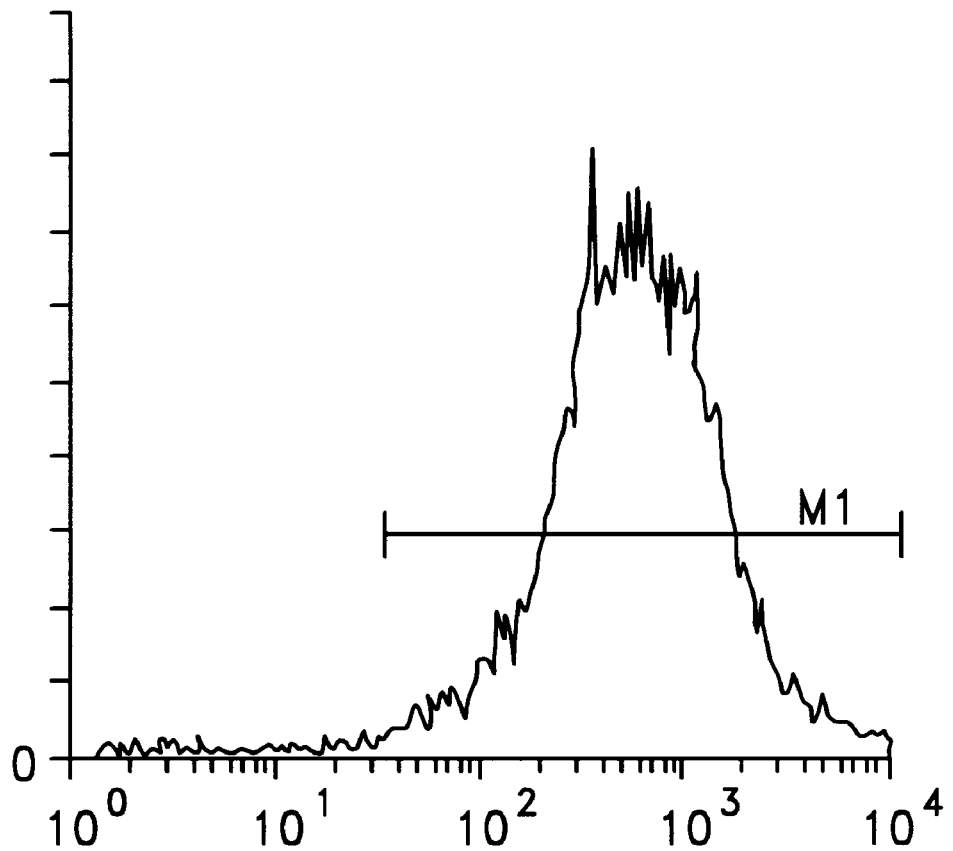
Figure 1D:
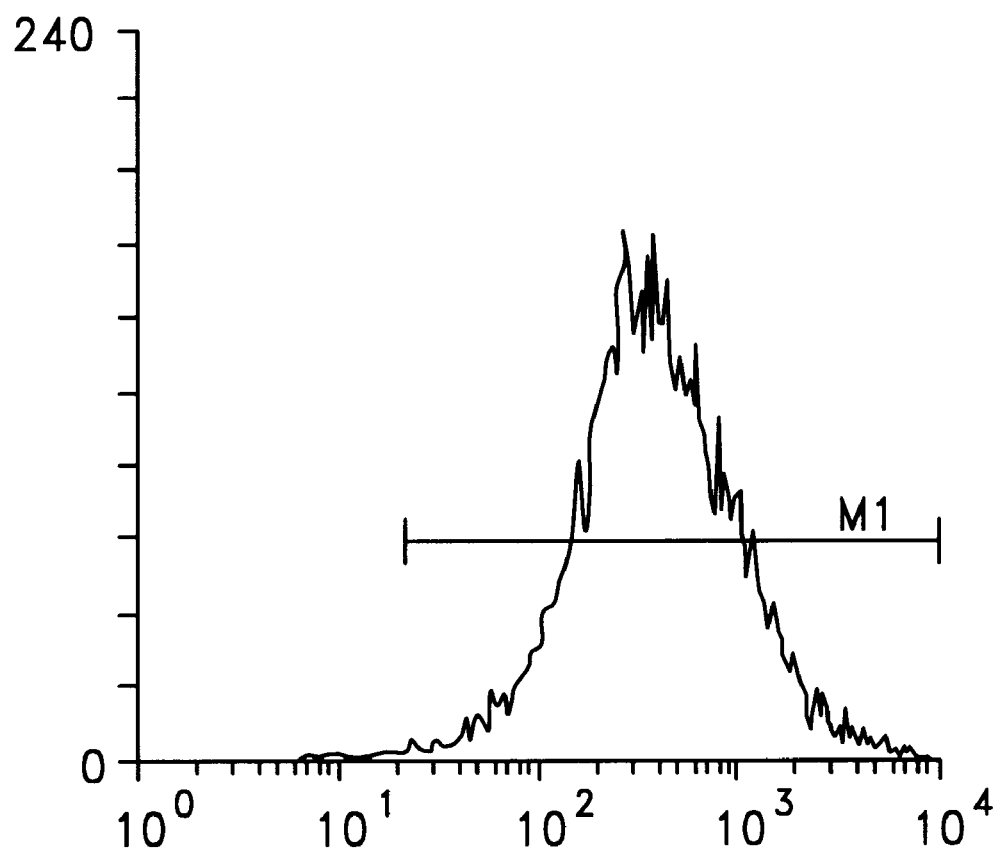

Representative FACS profiles are shown in FIGS. 1A–1D. A control mouse IgG did not label the cells (FIG. 1A), while a previously described MAb to gp120, 110.4 (FIG. 1B) labeled the cells strongly. The profiles of one new anti-gp120 MAb, D34, and one new anti-gp41 MAb, D6 are shown in FIGS. 1C and 1D, respectively. At least 80% of the MAbs against the oligomeric form of gp140 were clearly positive in this assay. Lack of reactivity could be due to a very low titer of antibody or reactivity with an epitope that is unique to the recombinant gp140 molecule. The fact that the large majority of the MAbs tested recognized native HIV-1 env provided strong evidence that the recombinant, oligomeric gp140 used here faithfully reflected the antigenic structure of the authentic molecule.

To determine which of the MAbs recognized linear, conformation-independent epitopes, each was screened for the ability to react with Western blotted gp140 that had been denatured and reduced prior to SDS-PAGE. Monoclonal antibodies that recognized protein that had been Western blotted in this fashion were judged to bind epitopes that were independent of the protein's conformation. The methods used to make these determinations are presented in Example 6.

EXAMPLE 6

Identification of MAbs that Bind Conformation-Independent Epitopes

Protein extracts from BS-C-1 cells infected with vaccinia virus recombinants that expressed different HIV-1 env genes from Example 2 were separated on SDS-PAGE (10%) and transferred to nitrocellulose membranes. In some cases, proteins were separated on preparative gels and the nitrocellulose was cut into 10 mm strips after protein transfer. The nitrocellulose membranes were incubated with anti-gp140 monoclonal antibodies (usually 1:5 dilution) for 1 hour at room temperature. After washing with PBS containing 0.2% Tween-20, the strips were incubated with $^{125}I$ labeled rabbit anti-mouse IgG for 30 minutes followed by washing. Hybridization with polyclonal antibody R160 was done at a 1:500 dilution followed by detection with $^{125}I$ Protein A. Proteins were visualized by autoradiography using standard, well known methods.

Representative results from this Western blotting protocol are summarized in Table 1. We found that 43% of the MAbs reacted strongly with denatured env, 11% reacted very weakly (e.g., D9, D59), and 46% were completely negative even though they efficiently immunoprecipitated env. We defined MAbs that reacted either very weakly or not at all to denatured env as conformation-dependent. The remaining MAbs, which reacted strongly with denatured env, were defined as conformation-independent. By this criteria, 57% (79/138) of the MAbs recognized conformationally sensitive epitopes while 43% (59/145) recognized linear or conformation-independent epitopes (Table 2). Of the 59 conformation-independent MAbs analyzed, 50 recognized epitopes in gp120 while 9 recognized epitopes in gp41 (Table 2).

TABLE 1

Binding Specificities of Anti-gp140 MAbs

| MAb | gp160 | gp120 | gp41 |
| --- | --- | --- | --- |
| M12 | − | − | − |
| D9 | + | − | − |
| D19 | +++ | +++ | − |
| D20 | − | − | − |
| D33 | − | − | − |
| D34 | +++ | +++ | − |
| D38 | − | − | − |
| D47 | +++ | +++ | − |
| D59 | + | − | − |
| T3 | +++ | − | +++ |
| T6 | − | − | − |
| T17 | +++ | +++ | − |
| T20 | − | − | − |
| T30 | +++ | − | +++ |
| 902 | +++ | + | − |
| Negative | − | − | − |
| R160 | +++ | +++ | +++ |

Thus, the immunization and screening approach that we have described generated a large number of MAbs that bind the env glycoprotein. The procedure described in Example 6 provided results that indicated which of the subunits of the env glycoprotein harbored epitopes that were recognized by the conformation-independent antibodies. Since less than half of all the MAbs that bound the env glycoprotein recognized conformation-independent epitopes, we expected the majority of the MAbs raised against the recombinant proteins to recognize conformation-dependent epitopes.

We used a protocol based on immunoprecipitation of metabolically labeled env glycoproteins to identify which of the subunits were recognized by the conformation-dependent epitopes. Example 7 describes the techniques used to produce radiolabeled env glycoprotein reagents that were used in these assays.

EXAMPLE 7

Metabolic Labeling and Isolation of env Glycoproteins

BS-C-1 cells were infected with recombinant vaccinia virus at a multiplicity of infection of 20. At 4 hours post infection, the virus inoculum was replaced with methionine-free minimal essential medium (MEM) containing 100 μCi [$^{35}$S]methionine/ml and incubated overnight. Cells were lysed in buffer containing 100 mM Tris-HCl pH 8.0, 100 mM NaCl, 0.5% TRITON-X-100. Soluble, secreted forms of env glycoprotein were obtained from the medium of infected cells. For preparation of the ectodomain fragment of gp41 (gp41s), the medium of infected cells was concentrated using Amicon microconcentrators and separated on a 5–20% sucrose gradient as described above. Monomeric gp120 was obtained from the medium of infected cells and in some cases was purified on a sucrose density gradient.

The epitope recognized by each MAb was initially mapped to either gp120 or the gp41 ectodomain. Mapping of the conformation-independent MAbs was done by Western blot analysis as described in Example 6. Mapping of the conformation-dependent MAbs was performed by immunoprecipitation analyses using several different metabolically labeled forms of env. These included monomeric gp120; a gradient purified gp41 ectodomain fragment derived from vCB-14; and a cell lysate containing full length gp160, gp120 and gp41.

Example 8 describes the immunoprecipitation protocol that was used to identify the subunit target of MAbs that did not stain Western blotted env proteins.

EXAMPLE 8

Mapping the Subunit Targets of MAbs that Recognize Conformation-Dependent Epitopes Immunoprecipitations were performed by incubating metabolically labeled env with various antibodies overnight at 4° C. Typically, 200 μl of a hybridoma culture supernatant or 1 μl of a polyclonal antiserum were used per immunoprecipitation. Where appropriate, 4 μg of rabbit anti-mouse IgG (Calbiochem) was then added for 30 minutes followed by 100 μl of a 200 protein A Sepharose suspension. After 30 minutes of rocking, the Sepharose beads were centrifuged at 1000× g for 4 minutes and the pellets were washed twice with 1 ml TRITON buffer (50 mM Tris-HCl pH 8.0, 300 mM NaCl, 0.1% TRITON-X-100). Proteins were eluted by boiling 5 minutes at 100° C. in sample buffer containing 5% 2-mercaptoethanol.

Table 2 presents a summary of monoclonal antibody reactivities that were raised against native, soluble, gp140. The MAb entries in the table are classified on the basis of which subunit they recognize (gp120 or gp41), whether they recognize conformation-dependent or conformation-independent epitopes, and by the original immunogenic target oligomeric form. Of the 79 conformation-dependent MAbs analyzed, 33 mapped to gp120. Many of these anti-gp120 MAbs coprecipitated gp41 in a lysate containing gp160, gp120, and gp41 whereas none of the anti-gp41 MAbs coprecipitated gp120. of the MAbs that did not immunoprecipitate purified gp120, many immunoprecipitated the purified gp41 ectodomain fragment indicating that their epitopes reside in the gp41 ectodomain. However, a number of MAbs were unable to immunoprecipitate either purified gp120 or the gp41 ectodomain fragment. Some of these MAbs immunoprecipitated both gp41 and gp160 from cell lysates. As a consequence, it was not possible to determine if these MAbs recognized gp160 specific epitopes and coimmunoprecipitated gp41, or whether they recognized oligomer dependent epitopes present in gp41. To distinguish between these possibilities, the MAbs were tested for their ability to immunoprecipitate a chimeric env protein consisting of HIV-2 gp120 and HIV-1 gp41 (vSC64). The vSC64 chimeric protein is transported to the cell surface and can mediate syncytia formation, indicating that it folds and assembles correctly. None of these MAbs immunoprecipitated the HIV-2 env protein. They did, however, recognize the chimeric protein, indicating that their epitopes are present in the HIV-1 gp41 ectodomain.

Thus, more than one-third of the MAbs derived from immunization with native oligomeric gp140 were directed against epitopes in the gp41 ectodomain. Comparison of the subunit mapping results with the data on conformation dependence revealed that the antigenic structure of gp41 is exquisitely sensitive to conformation. More than 80% (43/52) of the MAbs to gp41 recognized conformation-dependent epitopes (Table 2). By contrast, the antigenic structure of gp120 appeared to be less sensitive to env tertiary structure, since 42% (33/79) of the gp120 MAbs recognized conformational epitopes (Table 2).

TABLE 2

Summary of Reactivities of MAbs Raised Against Native, Soluble, gp140

| | Indep Total | Conf Dep Epitope | Conf Indep Epitope | CD4 V3 Loop | blocking |
|---|---|---|---|---|---|
| All Mabs | | | | | |
| Total | 138 | 59 | 79 | 15/82 | 19/76 |
| Conformation Dep | 79 | — | — | 0/32 | 19/49 |
| Conformation Indep | 59 | — | — | 15/50 | 0/27 |
| gp120 Mabs | | | | | |
| Total | 83 | 50 | 33 | 15/82 | 19/41 |
| Conformation Dep | 33 | — | — | 0/32 | 19/20 |
| Conformation Indep | 50 | — | — | 15/50 | 0/21 |
| gp41 Mabs | | | | | |
| Total | 52 | 9 | 43 | — | 0/35 |
| Conformation Dep | 43 | — | — | — | 0/29 |
| Conformation Indep | 9 | — | — | — | 0/6 |
| Immunogen-Monomer | | | | | |
| All Mabs | 15 | 9 | 6 | — | 3/12 |
| gp120 Mabs | 12 | 9 | 3 | 7/12 | 3/10 |
| gp41 Mabs | 3 | 0 | 3 | — | 0/2 |
| Immunogen-Dimer | | | | | |
| All Mabs | 68 | 19 | 49 | — | 14/41 |
| gp120 Mabs | 34 | 14 | 20 | 6/33 | 14/22 |
| gp41 Mabs | 31 | 5 | 26 | — | 0/19 |
| Immunogen-Tetramer | | | | | |
| All Mabs | 55 | 31 | 24 | — | 2/23 |
| gp120 Mabs | 37 | 27 | 10 | 2/37 | 2/9 |
| gp41 Mabs | 18 | 4 | 14 | — | 0/14 |

Example 9 describes the method used to more precisely map the env glycoprotein epitopes recognized by the MAbs. The approach we employed relied on the use of a series of recombinant env molecules that differed from each other by sequential deletions from the carboxy terminal end of the protein.

EXAMPLE 9

Detailed Epitope Mapping of MAbs

A series of C-terminally truncated env molecules expressed either by recombinant vaccinia viruses or by the transient vaccinia/T7 system described by Fuerst et al., in *Proc. Natl. Acad. Sci. USA* 83:8122 (1986), served as binding substrates for the MAbs. The env molecules used in this procedure included full length gp140 (678 amino acids), two molecules with sequential truncations in gp41 (635 and 574 amino acids), full length gp120 (502 amino acids), and three truncated forms of gp120 (393, 287, and 204 amino acids) as described by Earl et al., in *J. Virology* 65:31 (1991), and by Earl et al., in *AIDS Res. and Hum. Retro.* 9:589 (1993). Mapping of the conformation-independent MAbs was performed by Western blotting extracts of cells expressing the truncated env molecules. The results are summarized in Table 3. Of the 9 anti-gp41 MAbs tested, 1 mapped to amino acids 503–574, 5 mapped to amino acids 575–635, and 3 mapped to amino acids 636–678. Of the 50 anti-gp120 MAbs to conformation-independent epitopes, 32 mapped to the amino terminal 204 amino acids, 3 mapped to amino acids 205–287, and 15 mapped to amino acids 288–393. Somewhat surprisingly, no conformation-independent MAbs mapped to the C-terminal region of gp120 (between amino acids 394–502) even though antibodies to this region are abundant in human serum. One explanation for this finding is that the C-terminal region of gp120 is partially sequestered by interactions with adjoining env subunits or with gp41.

TABLE 3

| env truncation | Total # of Mabs | Total # of amino acids |
|---|---|---|
| gp120 | | |
| 1–204 | 32 | 204 |
| 205–287 | 3 | 83 |
| 288–393 | 15 | 106 |
| 394–502 | 0 | 109 |
| gp41 | | |
| 503–574 | 1 | 72 |
| 575–635 | 5 | 61 |
| 636–678 | 3 | 43 |

Initial mapping of the conformation-dependent MAbs was done by immunoprecipitation of metabolically labeled, truncated env molecules. Of the 39 anti-gp41 MAbs tested, 3 efficiently immunoprecipitated the 636 amino acid env molecule indicating that amino acids 635–678 are not necessary for antibody recognition. Of the 32 anti-gp120 antibodies tested, only 2 immunoprecipitated the 393 amino acid gp120 molecule; one of these also immunoprecipitated the 287 amino acid molecule. However, the inability of a conformation-dependent MAb to immunoprecipitate a truncated form of env does not necessarily imply that its epitope lies completely or even partially within the truncated area since the overall structure of the truncated molecules may be significantly different from the native, full length protein. To determine the fraction of MAbs directed against the gp120 V3 loop generated by immunization with oligomeric gp140, a V3 loop peptide ELISA assay was performed with both conformation-dependent and -independent anti-gp120 MAbs. Example 10 describes the method used to assess the ability of MAbs to recognize the V3 loop region of gp120.

EXAMPLE 10

Reactivity of MAbs with the V3 Loop Peptide

The HIV-1 IIIB V3-loop peptide (CNTRKSIRIQRGPGRAFVTIGK) (Seq. I.D. No: 5) (American Bio-Technologies, Cambridge, Mass.) and the HIV-1 MN V3-loop peptide (YNKRKRIHIGPGRAFYTTKNIIG) (Seq. I.D. No: 6) (NIAID, Biological Resources Branch) were used to determine the V3 loop reactivities of the MAbs. Briefly, the wells of IMMULON II 96 well assay plates were coated with 50 $\mu$l of 0.05 M sodium carbonate pH 9.5, containing 0.25 $\mu$g of peptide, overnight at 4° C. Plates were washed with PBS containing 0.1% Tween 20 and blocked with a solution of proteolyzed gelatin (Boehringer Mannheim Biochemicals). Antibody binding was performed at room temperature for 1 hour. Serial dilutions were tested in duplicate. Bound MAb was detected with a peroxidase-conjugated anti-mouse IgG (Boehringer Mannheim Biochemicals) and 2,2'-Amino-di-[3-ethylbenzthiazoline sulfonate] substrate (Boehringer Mannheim Biochemicals). All MAbs exhibiting binding were reexamined on mock-coated plates, and no false positives were detected.

We found that 15 of 50 conformation-independent MAbs exhibited reactivity with the HIV-1 IIIB V3 loop peptide (Table 2). Of these, two cross-reacted with a V3 loop peptide from the MN strain. Surprisingly, a correlation was observed between the oligomeric state of the immunogen used and the frequency with which anti-V3 loop MAbs were derived. Of the 15 MAbs derived from animals immunized with monomeric gp140, 7 were against the V3 loop. In contrast, only 6 of 32 MAbs from animals immunized with dimer and 2 of 38 immunized with tetramer bound to the V3 loop peptide (Table 2). Thus, a greater proportion of non-V3 loop MAbs was obtained when oligomeric gp140 was used as the immunogen indicating that the V3 loop may not be a predominant epitope when presented in the context of oligomeric gp140. For this reason, immunization with oligomeric gp140 may, as a consequence, generate a greater proportion of antibodies to conserved, conformational epitopes rather than to variable, linear regions of the protein.

Unlike antibodies to the V3 loop, neutralizing antibodies which block env-CD4 binding generally recognize conformationally sensitive epitopes and often recognize the env from divergent strains. We tested a large panel of MAbs to both gp120 and gp41 for the ability to block binding of sCD4 to env.

Example 11 describes the methods used to assay the abilities of different MAbs to block the env-CD4 interaction.

EXAMPLE 11

Ability of MAbs to Block env-CD4 Binding

Metabolically labeled gp140 and sCD4 were prepared from the medium of cells infected with vPE12B and vCB-5, respectively. Dimeric gp140 was purified by sucrose density gradient centrifugation as described above. 100 µl of hybridoma supernatant (MAb in excess of env) was incubated overnight at 4° C. with dimeric gp140. A small amount of sCD4 was added and incubated for 30 minutes at room temperature. Then 2 µg of rabbit anti-mouse IgG was added for 30 minutes, followed by 100 µl of Protein A Sepharose beads (20% suspension). After 30 minutes of gentle rocking, the beads were washed once with buffer containing 100 mM Tris-HCl pH 8.0, 100 mM NaCl, 0.5% TRITON-X-100 and samples were analyzed by SDS-PAGE (10%). MAb F105, which blocks CD4 binding, was used as a positive control for CD4 blocking activity. The MAb F105 was obtained from the AIDS Research and Reference Program. The anti-V3 loop MAb, 902, that does not block CD4 binding was used as a negative control in these procedures.

However, we discovered that of the 20 conformation-dependent anti-gp120 MAbs tested, 19 efficiently blocked sCD4 binding (Table 2). In contrast, none of the 21 conformation-independent anti-gp120 MAbs tested blocked CD4 binding. As expected, none of the anti-gp41 MAbs blocked binding of sCD4 regardless of their conformational dependence. Thus, in this panel of MAbs, the ability to block sCD4 binding was restricted to conformation-dependent antibodies that bound gp120. We have therefore discovered that antibodies raised against the oligomeric form of gp140 provide advantages in that they can efficiently block CD4/env interactions.

It is known that conformation-dependent epitopes typically represent highly conserved structural features of proteins. For this reason MAbs raised against the oligomeric structure of env proteins should bind epitopes common to a broad spectrum of HIV-1 strains. Such a class of MAbs will be particularly useful as diagnostic reagents. Example 12 illustrates how one of ordinary skill in the art can identify conformation-dependent MAbs that recognize the env epitopes common to a variety of HIV-1 strains.

EXAMPLE 12

Identification of Conformation-Dependent MAbs that Recognize a Broad Spectrum of HIV-1 Strains Human blood samples are taken from normal donors and individuals known to be infected with HIV-1. The infected blood samples have been previously typed, either by antibody staining or nucleic acid analysis, so that the strain of HIV-1 that is the infectious agent in each sample is identified. A panel of blood specimens is then chosen that includes a normal sample to be used as a negative control, and several additional samples that collectively represent infections by a variety of different HIV-1 strains. Aliquots of the blood samples are incubated with antibodies against oligomeric env. Methods for producing these antibodies are described in Example 3. Antibodies that are not specific for conformational epitopes are also included as controls. After incubation of approximately 30 minutes at 4° C., the cells are washed twice with PBS containing 1% bovine serum albumin, and incubated with a goat anti-mouse IgG antibody conjugated to fluorescein isothiocyanate for 30 minutes at 4° C. The cell samples are subsequently washed two additional times with PBS and then resuspended in 1 ml of 4% paraformaldehyde. These samples are then analyzed with a fluorescence-activated cell sorter (FACScan; Becton Dickinson). The fluorescence intensity observed for the normal control sample establishes the level of non-specific background labeling. In general, conformation-dependent MAbs bind to a wide range of HIV-1 strains, whereas non-conformational dependent antibodies only bind to one strain of HIV-1.

Given the identification of conformational-dependent MAbs that bind a broad range of HIV-1 strains, it then becomes advantageous to use these antibodies as reagents in immunoassays to identify HIV-1. These antibodies advantageously identify a wide range. of different HIV-1 strains. Such a protocol will provide a more accurate and inexpensive HIV-1 assay. An immunoassay conducted with a single MAb detection reagent will require fewer reagents and a lesser number of control samples to ensure assay reliability. Example 13 illustrates how the MAbs identified in Example 12 can be used to identify a patient having a HIV-1 infection.

EXAMPLE 13

Assay for the Presence of HIV-1 Antigens in Serum Samples

A blood sample drawn from a patient suspected of having a HIV-1 infection is centrifuged to produce a serum supernatant. Samples of the test serum are placed in wells of a 96-well microtiter plate. Control samples of serum from uninfected (negative control), and HIV-1 (positive control) infected individuals are placed in different wells of the microtiter plate. A MAb having specificity for oligomeric gp140, and identified as recognizing a variety of HIV-1 strains, is then added to all wells that contain control or test serum samples. After incubation for 1–2 hours at 37° C., the wells are washed three times with PBS. Alkaline phosphatase-conjugated goat anti-mouse IgG is then added to each of the sample wells. The plates are incubated at 37° C. for an additional hour, washed twice with PBS and incubated with p-nitrophenyl phosphate at 0.5 mg/ml in diethanolamine as a phosphatase substrate. Absorbance readings at 410 nm are then taken for all samples. The negative control has a low absorbance reading, and establishes a background reference. The positive control has a high absorbance reading and indicates that all reagents used in the assay are performing properly. Comparison of the absorbance readings obtained for the wells having the patient's serum with those from the positive and negative controls unambiguously indicates the presence or absence of HIV-1 antigens.

The recombinant gp140 oligomers produced according to the method of the present invention could also be useful as a vaccine for the prevention of HIV-1 infection. Since oligomeric gp140 glycoproteins elicit a humoral immune response skewed toward conformation-dependent epitopes, rather than conformation-independent epitopes, it is likely that such a response will be advantageously protective against a broad range of HIV-1 strains.

Example 14 illustrates one vaccination protocol that can be used to stimulate a humoral immune response against conformation-specific epitopes on HIV-1. Those of ordinary skill in the art will recognize that other methods for performing a vaccination are well known in the art.

EXAMPLE 14

Use of Recombinant HIV-1 env Glycoproteins as Immunogens in a Vaccine

Human subjects at risk of exposure to HIV-1 are vaccinated with sucrose gradient-purified gp140 env glycoprotein oligomers that are produced in a manner detailed in Example 2. These glycoprotein preparations are dialyzed against cold isotonic saline buffer prior to being assayed for protein concentration. The dialyzed subunit proteins are diluted to a final concentration range of 10–1000 µg/ml, and administered by injection together with a pharmaceutically acceptable carrier, such as phosphate bufferd saline. Injection of the glycoprotein immunogen is repeated once every 3 weeks, for a total of 4 injections. Immunizing doses of the gradient-purified env glycoprotein are determined in accordance with methods that are well known to those of ordinary skill in the art. Stimulation of an immune response in the patient is monitored by the appearance of anti-env antibodies in serum using standard techniques, such as ELISA, that are also known to those who are skilled in the art.

We have constructed a soluble, oligomeric form of the HIV-1 env glycoprotein which reflects native env structure sand elicits a diverse array of antibody reactivities, particularly antibodies to conformational epitopes. The repertoire of antibodies raised against oligomeric gp140 is qualitatively different than that previously raised against monomeric env. It is clear, for example, that env oligomeric structure has significant antigenic implications both in gp41 and gp120. The large number of MAbs we have generated against gp41, all of which immunoprecipitate native protein, should make it possible to construct a relatively detailed antigenic map of this subunit and to identify regions that are immunogenic, conserved and to which neutralizing antibodies are directed. These findings, coupled with observations that native gp140 elicits neutralizing antibodies more effectively than the denatured molecule, strongly argue that taking into account env oligomeric structure will be important in understanding the humoral response to HIV-1 infection and potentially for the design of env subunit preparations which can effectively elicit broadly cross reactive, neutralizing antibodies.

EXAMPLE 15

Use of Antibodies Against the Oligomeric Structure of gp140

A patient having a HIV infection is identified by standard, well known methods. Antibodies against the oligomeric form of gp140 are raised as described above. A pharmaceuticaly effective concentration of 1–10,000 µg/kg body weight of anti-gp140 are injected into the patient. A second (control) patient, suffering from a HIV infection, is injected with an antibody with specificity for a non-HIV epitope. After approximately 1 week, progress of the HIV infection is measured in each patient. The control patient has an increased progression of HIV infection as compared to the patient injected with the anti-gp140 antibodies.

We have constructed a soluble, oligomeric form of the HIV-1 env glycoprotein which reflects native env structure and elicits a diverse array of antibody reactivities, particularly antibodies to conformational epitopes. The repertoire of antibodies raised against oligomeric gp140 is qualitatively different than that previously raised against monomeric env. It is clear, for example, that env oligomeric structure has significant antigenic implications both in gp41 and gp120. The large number of MAbs we have generated against gp41, all of which immunoprecipitate native protein, should make it possible to construct a relatively detailed antigenic map of this subunit and to identify regions that are immunogenic, conserved and to which neutralizing antibodies are directed. These findings, coupled with observations that native gp140 elicits neutralizing antibodies more effectively than the denatured molecule, strongly argue that taking into account env oligomeric structure will be important in understanding the humoral response to HIV-1 infection and potentially for the design of env subunit preparations which can effectively elicit broadly cross reactive, neutralizing antibodies.

What is claimed is:

1. A method of producing neutralizing antibodies against conformational epitopes of HIV-1 envelope proteins in a human, comprising:

administering to a human a recombinant uncleaved gp140 protein retaining its oligomeric structure so that said human produces neutralizing antibodies against conformational epitopes of HIV-1 envelope proteins found on the oligomeric structure of said gp 140, said gp140 protein being defined as a C-terminally truncated form of HIV-1 gp160 protein that is missing the gp41 transmembrane domain.

2. The method of claim 1 wherein said administering step is selected from the group consisting of intradermal, intramuscular, intraperitoneal and intravenous administration.

3. The method of claim 1 further comprising the step of obtaining said gp140 protein by running said gp140 through lectin chromatography followed by a sizing gradient.

4. The method of claim 1 further comprising the step of obtaining said gp140 protein by running said gp140 through affinity chromatography with elution at pH8 followed by a sizing gradient.

5. The method of claim 1, 3 or 4 wherein said gp 140 protein is further defined as missing the gp120/gp41 cleavage site.

* * * * *